United States Patent [19]

Willner et al.

[11] 4,086,059
[45] Apr. 25, 1978

[54] METHOD FOR THE ANALYSIS OF THYROID HORMONES

[75] Inventors: Howard Willner, San Anselmo; Vito J. Mangiardi, Point Richmond, both of Calif.

[73] Assignee: Bio-Rad Laboratories, Inc., Richmond, Calif.

[21] Appl. No.: 578,247

[22] Filed: May 16, 1975

[51] Int. Cl.² ............................................. G01N 33/16
[52] U.S. Cl. ................................ 23/230.3; 23/230.6; 424/1; 250/303
[58] Field of Search ............... 23/230 B, 230.3, 230.6; 424/1, 1.5; 250/303, 304

[56] References Cited
U.S. PATENT DOCUMENTS

| 3,743,482 | 7/1973 | Eisentraut | 23/230.6 |
| 3,776,698 | 1/1972 | Eisentraut | 23/230.6 |
| 3,850,577 | 11/1974 | Ashkar | 23/230 B |

OTHER PUBLICATIONS

Dunn et al., *Clin. Chem.*, vol. 19, pp. 1063–1066, (1973).
Tabachnick, *J. Biol. Chem.*, vol. 239, pp. 1242–1249, (1964).

*Primary Examiner*—Robert M. Reese
*Attorney, Agent, or Firm*—Townsend and Townsend

[57] ABSTRACT

Method for competitive binding in diagnostic clinical testing for thyroid function in which blood serum is sufficiently acidified to inactivate binding of thyroid hormone to serum proteins. The serum test solution is then mixed directly with a buffered competitive binding protein solution without first separating inactivated endogenous serum proteins.

6 Claims, No Drawings

METHOD FOR THE ANALYSIS OF THYROID HORMONES

This invention relates to methods for determining thyroid function from a blood serum sample. In a preferred embodiment, it relates to a method for testing a blood serum sample for thyroid function employing a competitive binding procedure in which the serum thyroid hormone and radioactive thyroid hormone tracer compete for the available binding sites on an exogenous thyroid hormone competitive binding protein.

It has been known for some time that under the influence of acid thyroid hormones dissociate from their binders in biological systems. See, for example, Bismuth, J., Castay, M. and Lissitzky, Clin. Chim. Acta 35 (1971) 285-298 and Tabochnik, Milton, J. Biol. Chem., Vol. 239; 4 (1964) 1242-1249. It has been further recognized that this binding phenomenon is pH dependent as reported in U.S. Pat. No. 3,776,698. This latter patent describes a procedure for a thyroid hormone test of a serum sample by the same so-called competitive binding concept utilized in the present invention. Said referenced U.S. patent, in common with other prior competitive binding methods for the analysis of thyroid hormones, requires as an initial step the isolation of thyroid hormones from their serum associates. This isolation has been accomplished in various ways including solvent extraction, precipitation by heat or chemical agents, and in the case of the above-referenced patent adsorption of the thyroid hormones on a particulate substrate with eventual elution therefrom after separating the particulate substrate from the serum associates.

The present invention is based on the discovery that isolation of thyroid hormones from their serum binding proteins is not required. The present invention accordingly provides a method whereby serum is pre-treated with acid to an extent sufficient to inactivate the binding of thyroid hormone by serum thyroid hormone binding protein. The inactivation has been found to continue in the presence of a buffer at pH 8.6, which is usually considered to be the optimum pH of thyroid binding protein functionality. The solution is then, without first separating the inactivated serum thyroid hormone binding protein, directly combined with a buffered radioactive tracer-biological binder mixture in such proportions that a competitive protein binding equilibrium is effected according to well-known principles in the art. A dramatic simplification over the prior art procedures is thereby provided. The simplification involves both the elimination of materials and reagents utilized in the prior art isolation steps, and of most importance, involves the elimination of labor needed to carry out the prior art isolation procedures.

Following the competitive protein binding step, the solution can be further processed as desired and in accordance with prior assay procedures. For example, bound hormones may be separated from unbound hormones utilizing any of the variety of techniques of the prior art. Radioactivity of either the bound or unbound hormones may be counted and information concerning thyroid status derived therefrom. The invention is broadly applicable to determinations of thyroid hormone by a competitive binding procedure. Thus, the exogenous competitive binding protein may be thyroid hormone binding globulin as in U.S. Pat. No. 3,776,698 with the separation of bound from unbound hormone practiced as described therein. The procedure is equally applicable to a radioimmunoassay such as described in U.S. patent application Ser. No. 557,722, filed Mar. 12, 1975, now abandoned, for T-4 RADIOIMMUNOASSAY, or U.S. patent application Ser. No. 530,920, filed Dec. 9, 1974, now abandoned, for T-3 RADIOIMMUNOASSAY, where the competitive binding protein utilized is an appropriate antibody selective for the thyroid hormone being assayed.

In general, a serum sample test solution of any convenient size and dilution such as utilized in the prior art may be selected. Both 50 and 100 $\mu l$ serum samples have been found to be useful. This sample is initially adjusted by adding acid so as to create a sufficiently low acidic condition to inactivate the binding of the thyroid hormone by serum proteins. In general, the critical amount of acid will be reached when the sample solution pH is about 3 or lower (more acidic). Once a sufficient amount of acid has been utilized the addition of more acid will have no significant effect. The only limitation is that the amount of acid added should not be so great that serum components are precipitated or that the acid concentration is raised to such a level that cannot be conveniently buffered by the buffering capacity of the competitive binding mixture next encountered. As will be demonstrated, the appropriate pH conditions can be accomplished with various inorganic and organic acids. Preferred acids are strong mineral acids with hydrochloric acid being the acid of practical choice. Other acids that have been found to be effective are sulfuric acid, nitric acid, phosphoric acid, perchloric acid, formic acid and trichloracetic acid.

Inactivation of binding of thyroid hormone in the serum test solution will be complete in a few minutes at ambient temperature, usually not more than about five minutes. At that point, the test solution can be combined with exogenous thyroid hormone binding protein, radioactive isotope labelled thyroid hormone in a trace amount, and a buffer to permit competitive binding. In general, the pH in the competitive binding mixture should be that of the prior art with a preferred pH being about 8.6 in the solution after all components including the acidified serum test solution have been combined. The desired buffered condition may be obtained with various buffers such as phosphate and the like. Good results have been specifically obtained with Tris. Preferably, the buffer system is a barbital buffer. Generally, the buffer will produce the desired pH condition when present in the competitive binding solution at a concentration of 0.05–0.1 M.

The choice of the exogenous competitive binding protein will depend on the particular type of assay being pursued. In many cases the competitive binding protein will be thyroid binding globulin (TBG) as mentioned above. Where radioimmunoassay is involved the competitive binding protein is an appropriate antibody. The dilution of the competitive protein binding solution and the amount of competitive binding protein therein is adjusted to give the dose response desired and which will generally produce a linear curve from the data generated from the assay from thyroid serum standards. In general, the amount of competitive binding protein added should be sufficient to produce a response for thyroid hormone serum concentrations of 2–16 mcg per 100 ml. It is preferred to use sufficient competitive binding protein to yield a standard curve slope of 0.16 or greater, as derived from the formula:

$$\frac{cpm \text{ for } 6.15 \text{ mcg } T\text{-}4 - cpm \text{ for } 12.3 \text{ mcg } T\text{-}4}{cpm \text{ for } 6.15 \text{ mcg } T\text{-}4}$$

The effectiveness of the present method is demonstrated in a correlation study between it and the prior art procedure commercially available from Bio-Rad Laboratories, Inc., Richmond, California, and sold under the trademark TETRA-COUNT. This prior art procedure is more specifically described in copending application Ser. No. 364,564, filed May 29, 1973, now U.S. Pat. No. 3,947,564, for RADIOACTIVE DETERMINATION OF SERUM THYROXINE. The results of the correlation study involving a total of 54 samples yielded a correlation of 0.92. This correlation further included a comparison of total protein values on the same specimens and essentially no correlation was found.

The following procedure was used:

Reagents
   0.025 N HCl
   Normal control #2080[1]
   Hyper control #2351[2]
   Various standard sera of concentrations shown below
   Reagent X
     a. competitive binding protein (TBG)
     b. trace amount $I^{125}$ (100,000 cpm)
     c. 0.075 M sodium barbital, pH 8.6
Procedure

| Procedure | Sample | 0.025 M HCl | Reagent X |
|---|---|---|---|
| $Std_1$ | 0.1 ml | 0.5 ml | 3.5 ml |
| $Std_2$ | " | " | " |
| $Std_3$ | " | " | " |
| $Std_4$ | " | " | " |
| $Std_5$ | " | " | " |
| Control[1] | " | " | " |
| Control[2] | " | " | " |
| | Vortex or shake incubate for 5 min. | | Vortex - incubate for 15 min. Pour over ion exchange column - count eluate |

[1] #2080 is a normal control serum of a stated T-4 mcg % of 4.5 ± 0.4.
[2] #2351 is a hyper control serum of a stated T-4 mcg % of 9.0 ± 1.0.

The above procedure was used to generate the following data to illustrate this invention. Data obtained with the procedure of Ser. No. 364,564 is shown in parallel. All counts per minute (cpm) are on the eluate of the ion exchange columns.

| | Present Invention | | Procedure of U.S. Pat. Appl. Serial No. 364,564 | | |
|---|---|---|---|---|---|
| | Mcg% T-4 Iodine | cpm | | cpm | Mcg% T-4 Iodine |
| $Std_1$ | 10.4 | 29851 30117 | $Std_1$ | 47104 48390 | 10.4 |
| $Std_2$ | 8.1 | 33834 33263 | $Std_2$ | 53259 53291 | 8.1 |
| $Std_3$ | 6.5 | 35419 35060 | $Std_3$ | 59075 59208 | 6.5 |
| $Std_4$ | 3.3 | 39890 39771 | $Std_4$ | 73119 74558 | 3.3 |
| $Std_5$ | 1.65 | 41280 41354 | $Std_5$ | 81001 80426 | 1.65 |

| | | | Procedure of U.S. Pat. Appl. Serial No. 364,564 | | |
|---|---|---|---|---|---|
| Patient Serum Sample | cpm | Patient Serum Sample | cpm | Patient Serum Sample | cpm |
| 1 | 58254 | 16 | 68502 | 31 | 71342 |
| 2 | 55773 | 17 | 68091 | 32 | 71606 |
| 3 | 62723 | 18 | 72547 | 33 | 73037 |
| 4 | 70962 | 19 | 64150 | 34 | 64735 |
| 5 | 60735 | 20 | 67607 | 35 | 72133 |
| 6 | 59881 | 21 | 55095 | 36 | 71481 |
| 7 | 63443 | 22 | 52166 | 37 | 64383 |
| 8 | 67541 | 23 | 69244 | 38 | assay not completed |
| 9 | 68130 | 24 | 67299 | 39 | 69263 |
| 10 | 74104 | 25 | 74215 | 40 | 77380 |
| 11 | 70660 | 26 | 66510 | 41 | 69783 |
| 12 | 60979 | 27 | 66840 | 42 | 52040 |
| 13 | 68074 | 28 | 71587 | 43 | 71572 |
| 14 | 66390 | 29 | 65093 | 44 | 68392 |
| 15 | 70192 | 30 | 58188 | 45 | 70074 |
| 46 | 55384 | 51 | 64880 | | |
| 47 | 55796 | 52 | 73251 | | |
| 48 | 73361 | 53 | 56327 | | |
| 49 | 69560 | 54 | 70435 | | |
| 50 | 81855 | | | | |

| | cpm | | cpm | | cpm |
|---|---|---|---|---|---|
| #2080 Control | 70996 | blend of controls | 58724 | #2351 Control | 52251 |
| #2080 Control | 69287 | blend of controls | 58984 | #2351 Control | 52214 |

Present Invention

| Patient Serum Sample | cpm | Patient Serum Sample | cpm | Patient Serum Sample | cpm |
|---|---|---|---|---|---|
| 1 | 35780 | 16 | 37922 | 31 | 39719 |
| 2 | 33417 | 17 | 38973 | 32 | 38120 |
| 3 | 37030 | 18 | 39022 | 33 | 39216 |
| 4 | 39373 | 19 | 36588 | 34 | 37257 |
| 5 | 35624 | 20 | 38390 | 35 | 39476 |
| 6 | 37588 | 21 | 32463 | 36 | 39135 |
| 7 | 36964 | 22 | 33247 | 37 | 36741 |
| 8 | 38109 | 23 | 39038 | 38 | 35013 |
| 9 | 39190 | 24 | 37986 | 39 | 38544 |
| 10 | 39642 | 25 | 39279 | 40 | 39090 |
| 11 | 38438 | 26 | 37710 | 41 | 37937 |
| 12 | 36939 | 27 | 37243 | 42 | 33387 |
| 13 | 38403 | 28 | 38620 | 43 | 38553 |
| 14 | 38654 | 29 | 37848 | 44 | 37974 |
| 15 | 37518 | 30 | 35473 | 45 | 37295 |
| 46 | 33945 | 51 | 37924 | | |
| 47 | 34468 | 52 | 39456 | | |
| 48 | 38786 | 53 | 33307 | | |
| 49 | 39511 | 54 | 38310 | | |
| 50 | 40956 | | | | |

| | cpm | | cpm | | cpm |
|---|---|---|---|---|---|
| #2080 control | 38734 | blend of controls | 35800 | #2351 control | 33067 |
| #2080 control | 38804 | blend of controls | 36224 | #2351 control | 32535 |

A determination of total protein on the above fifty samples and controls was done by the Biuret reaction of Henry, Sobel, and Berkman, ref. 2665, page 182, Clinical Chem. Principles and Techniques, Richard J. Henry. T-4 values from the preceding work is also shown. The results are as follows:

| Sample | Present Invention - mcg% T-4 iodine | S.N.364,564 mcg % T-4 iodine | Total protein g protein/100 ml serum |
|---|---|---|---|
| 1 | 6.3 | 6.8 | 6.4 |
| 2 | 8.0 | 7.5 | 8.0 |
| 3 | 5.4 | 5.7 | 6.9 |
| 4 | 3.7 | 3.9 | 7.6 |
| 5 | 6.4 | 6.2 | 7.5 |
| 6 | 5.0 | 6.4 | 6.8 |
| 7 | 5.4 | 5.5 | 7.1 |
| 8 | 4.6 | 4.6 | 6.8 |
| 9 | 3.8 | 4.5 | 6.9 |
| 10 | 3.5 | 3.2 | 6.5 |
| 11 | 4.4 | 3.9 | 7.0 |
| 12 | 5.5 | 6.1 | 7.0 |
| 13 | 4.4 | 4.5 | 6.5 |
| 14 | 4.2 | 4.9 | 7.1 |
| 15 | 5.1 | 4.0 | 6.0 |
| 16 | 4.8 | 4.4 | 7.3 |
| 17 | 4.0 | 4.5 | 8.6 |
| 18 | 4.0 | 3.5 | 7.1 |
| 19 | 5.7 | 5.4 | 7.5 |
| 20 | 4.4 | 4.6 | 7.1 |
| 21 | 8.7 | 7.6 | 6.4 |
| 22 | 8.1 | 8.6 | 6.5 |
| 23 | 4.0 | 4.3 | 7.0 |
| 24 | 4.7 | 4.7 | 6.8 |
| 25 | 3.8 | 3.2 | 7.0 |
| 26 | 4.9 | 4.8 | 7.5 |
| 27 | 5.3 | 4.8 | 6.3 |
| 28 | 4.3 | 3.7 | 7.5 |
| 29 | 4.8 | 5.1 | 6.9 |

-continued

| Sample | Present Invention - mcg% T-4 iodine | S.N.364,564 mcg % T-4 iodine | Total protein g protein/100 ml serum |
|---|---|---|---|
| 30 | 6.5 | 6.8 | 7.0 |
| 31 | 3.5 | 3.8 | 8.4 |
| 32 | 4.6 | 3.7 | 6.8 |
| 33 | 3.8 | 3.4 | 7.9 |
| 34 | 5.2 | 5.2 | 6.5 |
| 35 | 3.6 | 3.6 | 6.8 |
| 36 | 3.9 | 3.7 | 7.2 |
| 37 | 5.6 | 5.3 | 6.7 |
| 38 | 6.8 | assay not completed | |
| 39 | 4.3 | 4.3 | 7.0 |
| 40 | 4.0 | 2.5 | 6.7 |
| 41 | 4.8 | 4.2 | 7.8 |
| 42 | 8.0 | 8.7 | 7.8 |
| 43 | 4.3 | 3.8 | 6.9 |
| 44 | 4.7 | 4.4 | 6.2 |
| 45 | 5.2 | 4.1 | 6.8 |
| 46 | 7.7 | 7.5 | 6.9 |
| 47 | 7.2 | 7.4 | 7.2 |
| 48 | 4.2 | 3.3 | 7.2 |
| 49 | 3.6 | 4.2 | 5.8 |
| 50 | 2.6 | 1.4 | 7.2 |
| 51 | 4.8 | 5.2 | 6.6 |
| 52 | 3.7 | 4.3 | 6.7 |
| 53 | 8.1 | 7.3 | 7.4 |
| 54 | 4.5 | 4.0 | 7.3 |
| #2080 control | 4.2, 4.2 | 3.9, 4.2 | |
| #2351 control | 8.7, 8.7 | 8.6, 8.6 | |
| Blend of controls | 6.3, 6.0 | 6.4, 6.3 | |

Excellent correlation with the immunoassay procedures of said above-referenced copending patent applications Ser. No. 530,920 (T-3) and Ser. No. 557,722 (T-4) have been obtained. In these experiments, the present acid inactivation replaced the bentonite adsorbent of Ser. No. 557,722 and the displacing agent of Ser. No. 530,920.

What is claimed is:

1. In a competitive binding procedure to determine the status of serum thyroid hormone in which a serum test solution is processed to separate the thyroid hormone from thyroid hormone binding protein prior to the competitive binding step, the improvement consisting essentially of adjusting the pH of the serum test solution to about 3 or lower essentially with an acid selected from the group consisting of hydrochloric acid, sulfuric acid, nitric acid, phosphoric acid, perchloric acid, formic acid and trichloracetic acid, and then admixing it directly with a solution containing exogenous thyroid hormone binding protein, radioactive isotope labelled thyroid hormone and buffer to execute said competitive binding step at a pH of about 8.6.

2. The improved competitive binding procedure in accordance with claim 1 wherein the pH of the serum test solution is adjusted with the addition of a strong mineral acid.

3. The improved competitive binding procedure in accordance with claim 2 wherein said strong mineral acid is hydrochloric acid.

4. A T-4 thyroid hormone clinical diagnostic test comprising: providing a test solution containing a serum sample having T-4 thyroid hormone bound to the serum proteins, adding sufficient reagent consisting essentially of a strong mineral acid to said test solution to inactivate the binding of T-4 thyroid hormone by endogenous serum thyroid hormone binding protein, combining the components of said acidified solution including unbound T-4 thyroid hormone and inactivated endogenous thyroid hormone binding protein with a buffered solution containing exogenous thyroid hormone binding protein and radioactive isotope labelled thyroid hormone tracer so as to cause competitive binding of said unbound T-4 thyroid hormone and T-4 radioactive tracer with said exogenous thyroid hormone binding protein at a pH of about 8.6, separating said competitive binding solution into a fraction containing T-4 thyroid hormone bound by said exogenous thyroid hormone binding protein and a fraction containing T-4 thyroid hormone not bound by said exogenous thyroid hormone binding protein, and determining the magnitude of radioactivity of at least one of said two fractions.

5. A T-4 thyroid hormone diagnostic test in accordance with claim 4 wherein the acid added to inactivate binding of T-4 thyroid hormone by endogenous thyroid hormone binding protein is hydrochloric acid and wherein the acid is added so as to create a pH of about 1-3 in the test solution.

6. A T-4 thyroid hormone diagnostic test in accordance with claim 4 wherein said buffered solution is a barbital buffered solution containing sufficient buffering ions to create a pH of about 8.6 in solution after combination of the acidified test solution and buffered solution.

* * * * *